United States Patent
Kiesele et al.

(10) Patent No.: US 7,364,552 B2
(45) Date of Patent: Apr. 29, 2008

(54) MEASURING SYSTEM FOR THE DETERMINATION OF THE CONCENTRATION OF PROPOFOL (2,6-DIISOPROPYLPHENOL) IN THE RESPIRATORY FLOW

(75) Inventors: Herbert Kiesele, Lübeck (DE); Andreas Hengstenberg, Lübeck (DE); Alex Martin Zbinden, Bern (CH); Rolf Lauber, Schuepfen (CH)

(73) Assignee: Drägerwerk Aktiengesellschaft, Lübeck (DE)

( * ) Notice: Subject to any disclaimer, the term of this patent is extended or adjusted under 35 U.S.C. 154(b) by 643 days.

(21) Appl. No.: 10/870,820

(22) Filed: Jun. 17, 2004

(65) Prior Publication Data
US 2005/0022811 A1 Feb. 3, 2005

(30) Foreign Application Priority Data
Aug. 1, 2003 (DE) ................. 103 35 236

(51) Int. Cl.
*A61B 5/08* (2006.01)
*A61M 16/00* (2006.01)
*A62B 7/00* (2006.01)

(52) U.S. Cl. ................. 600/532; 128/204.18

(58) Field of Classification Search .................
128/203.12–203.14, 203.18, 203.22, 203.25,
128/204.18, 204.23; 600/529, 538, 531–533;
73/23.3; 204/431–432, 409
See application file for complete search history.

(56) References Cited

U.S. PATENT DOCUMENTS

| | | | |
|---|---|---|---|
| 6,265,750 B1 * | 7/2001 | Feng et al. ................. | 257/414 |
| 6,439,231 B1 * | 8/2002 | Fukunaga et al. ..... | 128/207.14 |
| 6,745,771 B2 * | 6/2004 | Castor et al. .......... | 128/205.27 |
| 6,981,947 B2 * | 1/2006 | Melker ...................... | 600/532 |
| 2003/0139681 A1 | 7/2003 | Melker et al. | |

FOREIGN PATENT DOCUMENTS

GB 2 353 363 A * 2/2001

OTHER PUBLICATIONS

A. Quattara et al., Target-controlled infusion of propofol and remifentanil in cardiac anaesthesia: influence of age on predicted effect-site concentrations, *British Journal of Anaesthesia*, 90 (5): pp. 617-622, 2003.

* cited by examiner

*Primary Examiner*—Teena Mitchell
*Assistant Examiner*—Kristen C. Matter
(74) *Attorney, Agent, or Firm*—McGlew and Tuttle P.C.

(57) ABSTRACT

A rapid measuring system for the determination of the concentration of propofol in the respiratory flow, which can be designed in a compact form, has the features of a breathing gas line (1) including a breathing gas sensor (2) detecting the respiration, wherein the breathing gas sensor (2) is connected to an evaluating unit (3), a propofol sensor (5) with a downstream pump (6) is in gas flow connection with the breathing gas line (1), wherein the evaluating unit (3) is connected with the propofol sensor (5) and the pump (6), so that the evaluating unit (3) actuates the pump (6) for breathing gas sampling depending on the signal of the breathing gas sensor (2), and the propofol sensor (5) sends a measured signal for the concentration of propofol in the breathing gas to the evaluating unit (3).

16 Claims, 2 Drawing Sheets

MEASURING SYSTEM FOR THE DETERMINATION OF THE CONCENTRATION OF PROPOFOL (2,6-DIISOPROPYLPHENOL) IN THE RESPIRATORY FLOW

CROSS REFERENCE TO RELATED APPLICATIONS

This application claims the benefit of priority under 35 U.S.C. § 119 of German patent application DE 103 35 236.8 filed Aug. 1, 2003 the entire contents of which are incorporated herein by reference.

FIELD OF THE INVENTION

The present invention pertains to a measuring system for the determination of the concentration of propofol (2,6-diisopropylphenol) in a respiratory flow.

BACKGROUND OF THE INVENTION

Besides the desired effects, adverse side effects must also be taken into consideration in connection with the administration and dosing of anesthetics. For example, an anesthetic overdosage may have fatal consequences; on the other hand, underdosing, associated with traumatic perceptions on the part of the patient, are likewise undesired. It is therefore of great interest to monitor the current concentration of the active ingredients in the patient's body and to effectively control it, if necessary, in the course of the anesthesia.

Even though monitoring of the concentration in the breathing gas of the patient is state of the art in the case of volatile anesthetics, and the expiratory concentration of the anesthetic gas is used as an indicator for the assessment of the anesthetic action, no comparable functioning measuring systems are known for the nonvolatile anesthetics administered intravenously and especially propofol.

Based on the rapid redistribution and metabolism of propofol in the patient's body, this anesthetic must be redosed continuously in order to maintain a constantly effective concentration. The dosing has been hitherto performed either according to preset dosing schemes or by means of microprocessor-controlled injection pumps, which infuse the drug on the basis of pharmacokinetic data (TCI=Target Controlled Infusion); see, e.g., the journal British Journal of Anaesthesia, 90 (5), pp. 617 to 623 (2003), A. Quattara et al.: Target-controlled infusion of propofol and remifentanil in cardiac anaesthesia: influence of age on predicted effect-site concentrations. The dosing by means of "TCI" is inaccurate according to this reference, especially in older patients.

The control of anesthesia according to the state of the art is thus based only on the predictions of a model rather than on actual concentration determinations at the patient. Considerable deviations occur here between the assumed concentration and the actual concentration in the patient, and there is, e.g., an anesthetic overdosage with the associated adverse cardiovascular effects such as a drop in blood pressure.

The rapid, direct determination of the current propofol concentration in the patient, associated with the possibility of controlling the propofol concentration by varying the rate of infusion, is not possible with the complicated laboratory methods known so far, such as liquid chromatography.

SUMMARY OF THE INVENTION

The object of the present invention is to provide a rapid measuring system that is easy to handle for the determination of propofol, specifically the active ingredient 2,6-diisopropylphenol, in the breathing gas, which is, moreover, part of a measuring and control circuit for the accurate intravenous dosing of a nonvolatile anesthetic such as propofol in a variant of the present invention.

The object is accomplished by introducing a measuring system for the determination of the concentration of propofol (2,6-diisopropylphenol) in the respiratory flow with a breathing gas line and with a breathing gas sensor determining the respiration, wherein the breathing gas sensor is connected to an evaluating unit. A propofol sensor is provided that is in gas flow connection with the breathing gas line. The propofol sensor has a downstream pump. The evaluating unit is connected with the propofol sensor and the pump, so that the evaluating unit actuates the pump for sampling breathing gas depending on the signal of the breathing gas sensor. The propofol sensor sends a measured signal for the concentration of propofol to the evaluating unit.

Compared with prior-art laboratory methods, the subject of the present invention makes it advantageously possible to determine the very low propofol concentrations that occur in the ppb (parts per billion) range and without the need for complicated apparatus, rapidly, in less than one minute, and the procedure can be applied in practice in the operating room and the intensive care unit alike. The measuring system according to the present invention, designed in a compact form as a portable measuring unit, can be transported with ease or, as the case may be, it can be integrated in an anesthesia workplace.

The measuring system as described above may provide the propofol sensor as an electrochemical gas sensor. Advantageously a measuring electrode may be used made of diamond-like carbon.

The propofol sensor may also be a SAW (Surface Acoustic Wave) sensor, an ion mobility spectrometer, a gas chromatograph, a mass spectrometer or a combination of a gas chromatograph and an ion mobility or mass spectrometer.

An adsorption filter with a heating means may be arranged upstream of the propofol sensor. With this, the sensitivity and the selectivity of the propofol measurement are increased by means of thermodesorption and measurement over a plurality of breaths.

Furthermore, a measuring system as described above may be provided in which the measuring electrode can be switched on and off at points in time preset by the evaluating unit. A mediator, which reacts selectively with propofol (2,6-diisopropylphenol) and forms a reaction product that accumulates over one or more breaths and whose concentration is determined electrochemically at the measuring electrode, may be added to the electrolyte of the electrochemical gas sensor.

The breathing gas sensor may be a $CO_2$, $O_2$ volume flow or temperature sensor, so that depending on the measured signal of the breathing gas sensor, which is characteristic of the properties of the respiratory flow. Reproducible breathing gas samples may be delivered into the propofol sensor from the respiratory flow for actuating the pump.

The breathing gas sensor may receive respiration parameters of the respiration unit of an anesthesia apparatus or respirator. A pump is actuated for breathing gas sampling via the evaluating unit especially such that the propofol sensor measures the end tidal propofol concentration in the respiratory flow breathed out.

Additionally, the evaluating unit may be connected to one or more dosing devices for the intravenous administration of propofol as a function of the current measured signal of the propofol sensor.

The evaluating unit may be provided with minima and/or maxima for the dosing of the total quantity of propofol and/or per unit of time for a patient.

Two exemplary embodiments will be described below on the basis of the two schematic figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
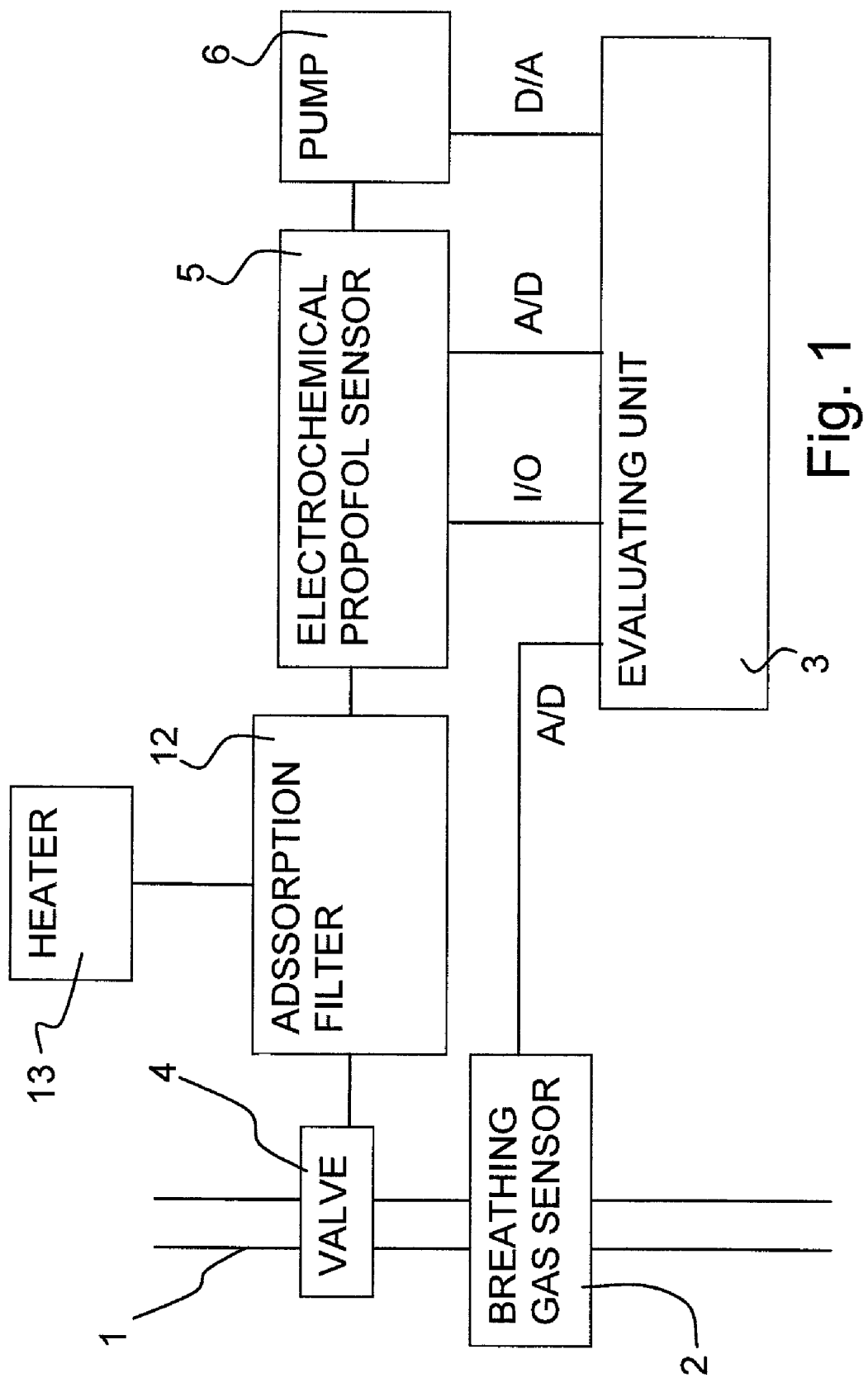
FIG. 1 is a schematic view of a measuring system for determining propofol in the respiratory flow.

The measuring system according to FIG. 1 has the following main components: The respiratory flow of a patient being treated with the intravenous anesthetic propofol is drawn off in a breathing gas line 1, the said breathing gas line 1 comprising the main stream or a side stream of the breathing gas flow. Via a branch 4, e.g., with a shut-off valve to the breathing gas line 1, the breathing gas line 1 is in gas flow connection with the propofol sensor 5 and with a downstream pump 6 for sampling breathing gas. A breathing gas sensor 2, which is connected, just as the propofol sensor 5 and the pump 6, to an evaluating unit 3, is additionally located in the breathing gas line 1.

As an alternative, the breathing gas sensor 2 receives respiration parameters of the respiration unit of an anesthesia apparatus or respirator and actuates the pump 6 such that the propofol sensor 5 measures, e.g., the end tidal propofol concentration in the respiratory flow breathed out. The mode of operation of the measuring system is such that depending on the measured signal of the breathing gas sensor 2, which is especially a CO2 sensor, the pump 6 is actuated by the evaluating unit, so that samples reproducible in respect to the propofol content, especially of alveolar air, are delivered for the propofol measurement from the respiratory flow.

The pump 6 may be preferably controlled by the evaluating unit 3 such that when a defined CO2 concentration, which is stored in the evaluating unit 3, is exceeded during the phase of expiration, the pump 6 is switched on, and it is switched off again when the current value is below a defined, stored CO2 concentration. Thus, a breathing gas sample is taken for the propofol measurement in a defined manner only during the phase of expiration.

As an alternative, the CO2 concentration may be measured continuously in the respiratory flow and related to the propofol concentration measured previously. The measurement of the propofol concentration proper or of its active ingredient, 2,6-diisopropylphenol, in the breathing gas sample being delivered by the pump 6 is preferably performed with a propofol sensor 5 embodied as an electrochemical gas sensor with a measuring electrode, which is made especially from diamond-like carbon.

The electrochemical gas sensor is equipped with a porous Polytetrafluoroethylene (PTFE) membrane arranged in front of the electrodes or is, in particular, also without such a membrane. The use of electrodes from doped diamond, carbon, gold, platinum or iridium is also possible, but is associated with a lower measurement selectivity and a higher detection limit.

An electrochemical gas sensor with a measuring electrode made of diamond-like carbon is described in DE 199 39 011 C1. Sulfuric acid or lithium chloride is preferably used as the electrolyte in this case. The measured signal of the electrochemical gas sensor is an indicator of the concentration of the measured analyte, here propofol or the active ingredient 2,6-diisopropylphenol.

Using the electrochemical gas sensor designed as described, which was used as a propofol sensor 5, it was also possible to measure surprisingly well the comparatively low propofol concentrations in the ppb range with high accuracy and low cross sensitivity to other components of the respiratory flow, such as CO2, CO, alcohol, and acetone. The propofol or 2,6-diisopropylphenol concentration in the breathing gas is measured with this measuring system.

The propofol concentrations in the patient's blood can be calculated from this by calculation with algorithms stored in the evaluating unit 3. The calculated values can be used further to control the dosing of propofol by means of intravenous administration in the patient after comparison with set points stored in the evaluating unit 3.

The propofol sensor 5 may also be designed as a SAW (Surface Acoustic Wave) sensor, as an ion mobility spectrometer, as a gas chromatograph, as a mass spectrometer or as a combination of a gas chromatograph and an ion mobility or mass spectrometer for the measurement of the propofol concentration in the respiratory flow.

Preliminary measurements with an ion mobility spectrometer have shown that 2,6-diisopropylphenol can be detected in the respiratory flow by a specific measured signal, so that selective detection of propofol in the air and breathing air is possible.

To increase the sensitivity and the selectivity of the measurement, an adsorption filter 12, made, e.g., of Tenax or activated carbon with a heating means in the form of a heater 13, may be arranged upstream of the propofol sensor 5, so that the propofol measurement can be improved by means of thermosorption after measurement over several breaths by enriching propofol in the measuring gas sample.

In case of the preferred use of an electrochemical gas sensor with a mediator in the electrolyte and with a measuring electrode made of diamond-like carbon, which is directly exposed to the breathing gas to be measured, the measuring electrode is switched off and then on by the evaluating unit 3 at predetermined points in time, so that a reaction product that is accumulating over one breath or preferably a plurality of breaths and can be measured as an averaged product is formed in the gas sensor, and the concentration of this reaction product is determined more accurately by means of the measuring electrode, the concentration being proportional to the concentration of propofol or the active ingredient 2,6-diisopropylphenol.

The mediator in the electrolyte is a substance such as compounds containing tetravalent cerium, which reacts with the analyte propofol so selectively that the reaction product formed can be electrochemically detected.

Figure 2:
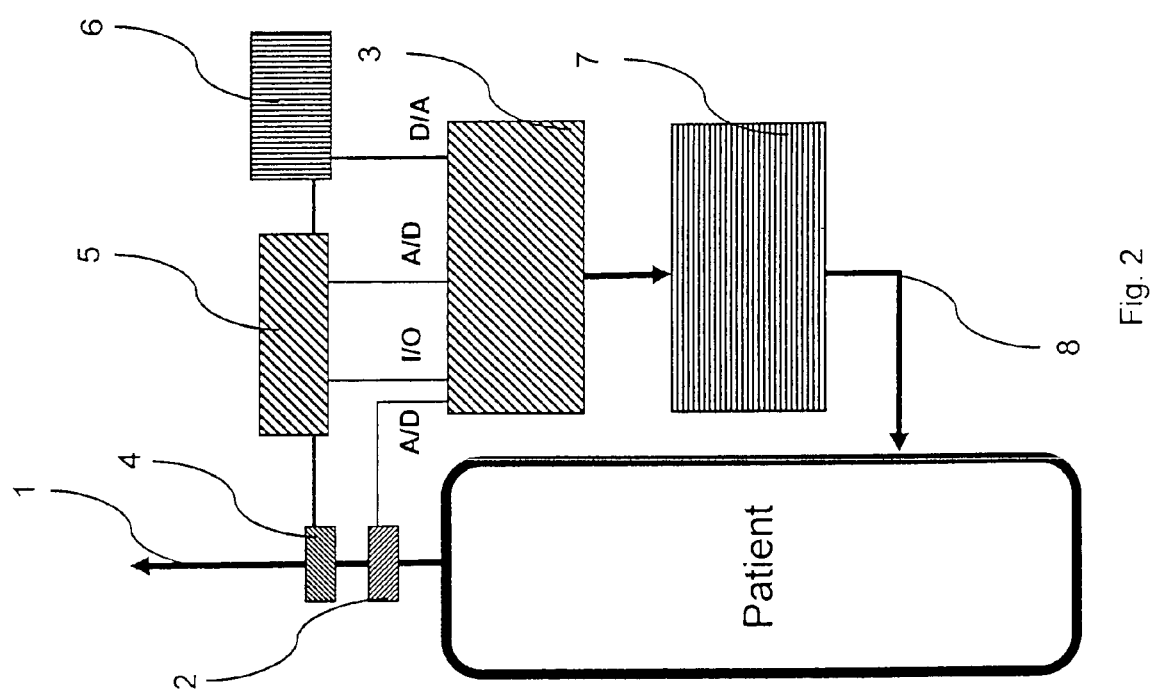
FIG. 2 is a schematic view of the expansion of a measuring system for determining propofol in the respiratory flow into a measuring and control circuit for the intravenous dosing of propofol.

FIG. 2 shows the expansion of a measuring system according to FIG. 1 to a measuring and control device with A/D and D/A converters for the intravenous dosing of propofol.

A breathing gas sample of a patient is taken from the breathing gas line 1 via the branch 4 by means of the pump 6 actuated by the evaluating unit 3 on the basis of a signal from the breathing gas sensor 2.

The propofol sensor 5 designed specifically as an electrochemical gas sensor is used to determine the propofol concentration in the breathing gas. The particular propofol concentration measured currently is converted in the evaluating unit 3 into the particular corresponding propofol concentration in the patient's blood by means of stored algorithms and compared with corresponding, especially patient-specific set points.

In case of deviation from a set point, the rate of dosing, i.e., the rate of infusion is increased or decreased for supplying the intravenous anesthetic propofol for the patient via the metering unit 7, which comprises, for example, one or more electrically actuated injection pumps, with an infusion line 8 to the patient, the said increase or decrease being adapted to the deviation.

The time-dependent changes in the propofol concentration are monitored by a repeated propofol measurement in the breathing gas, and the dosing of propofol is adapted, if necessary, by the expanded measuring and control system.

Besides the polling of the propofol measured signal, the measuring and control system may be expanded by additional control variables, which are based on, e.g., physiological or neurological parameters of the patient in a suitable hierarchy.

The evaluating unit 3 is optionally provided with minima and/or maxima for the propofol concentration and consequently also for the dosing of propofol as a whole and/or per unit of time for the particular patient being treated in order to avoid an extreme underdosing with the inadequate anesthesia associated therewith and or an extreme overdosage with the complications associated therewith.

While a specific embodiment of the invention has been shown and described in detail to illustrate the application of the principles of the invention, it will be understood that the invention may be embodied otherwise without departing from such principles.

What is claimed is:

1. A method for determining the concentration of propofol (2,6-diisopropylphenol) in a respiratory flow, the method comprising:
providing a breathing gas line;
providing an evaluating unit;
providing a breathing gas sensor in fluid connection with said breathing gas line and connected to said evaluating unit;
determining a parameter of respiratory flow using said gas sensor and transmitting a signal to said evaluating unit related to the determined parameter;
providing a propofol sensor in fluid connection with said breathing gas line and connected to said evaluating unit, wherein said propofol sensor is an electrochemical gas sensor with a measuring electrode made of diamond-like carbon;
providing a pump in fluid connection with said propofol sensor, downstream of said propofol sensor for drawing a gas sample from said breathing gas line through said propofol sensor;
actuating said pump by said evaluating unit for sampling breathing gas; and
transmitting a measured signal for a concentration of propofol from said propofol sensor to said evaluating unit.

2. A method in accordance with claim 1, wherein an adsorption filter with a heating means is arranged upstream of said propofol sensor enriching propofol in the gas sample.

3. A method in accordance with claim 1, wherein said measuring electrode can be switched on and off at points in time preset by said evaluating unit, and a mediator, which reacts selectively with propofol (2,6-diisopropylphenol) and forms a reaction product that accumulates over one or more breaths and whose concentration is determined electrochemically at said measuring electrode, is added to an electrolyte of said electrochemical gas sensor.

4. A method in accordance with claim 1, wherein said breathing gas sensor is a sensor of at least one of $CO_2$, $O_2$ volume flow or temperature sensor, so that depending on a measured signal of said breathing gas sensor, which is a property of a respiratory flow, reproducible breathing gas samples are delivered into said propofol sensor from said respiratory flow for actuating said pump.

5. A method in accordance with claim 1, wherein said breathing gas sensor receives a respiration parameter of a respiration unit of an anesthesia apparatus or respirator and actuates said pump for breathing gas sampling via said evaluating unit especially such that said propofol sensor measures an end tidal propofol concentration in a respiratory flow breathed out.

6. A method in accordance with claim 1, wherein said evaluating unit is connected to at least one dosing device for an intravenous administration of propofol as a function of a current measured signal of said propofol sensor.

7. A method in accordance with claim 6, wherein said evaluating unit is provided with minima and/or maxima for a dosing of a total quantity of propofol and/or per unit of time for a patient.

8. A measuring system for determining the concentration of propofol (2,6-diisopropylphenol) in a respiratory flow, the measuring system comprising:
a breathing gas line;
an evaluating unit;
a breathing gas sensor comprising at least one of a $CO_2$ sensor, an $O_2$ sensor, a volume flow sensor and a temperature sensor, said breathing gas sensor issuing a measured signal corresponding to a parameter of respiratory flow indicating an expiratory phase of a respiratory flow, said breathing gas sensor being connected to said breathing gas line and to said evaluating unit, wherein said breathing gas sensor transmits said measured signal to said evaluating unit;
an electrochemical propofol sensor comprising a measuring electrode made of one of diamond-like carbon, doped diamond, carbon, gold, platinum and iridium, said propofol sensor being in gas flow connection to said breathing gas line and being connected to said evaluating unit; and
a pump connected to said propofol sensor, said evaluating unit activating said pump for obtaining a sample of breathing gas based on an indicated expiratory phase of the respiratory flow, said propofol sensor sending a propofol measured signal to said evaluating unit corresponding to a concentration of propofol in the sample of breathing gas, wherein said electrochemical propofol sensor comprises electrodes including said measuring electrode and an electrolyte, said electrolyte comprising sulfuric acid or lithium chloride and said electrolyte including a mediator comprising one or more compounds containing tetravalent cerium which reacts selectively with propofol (2,6-diisopropylphenol) and forms a reaction product that accumulates over one or more samples, said reaction product being determined electrochemically at said measuring electrode.

9. A measuring system for determining the concentration of propofol (2,6-diisopropylphenol) in a respiratory flow, the measuring system comprising:
   a breathing gas line;
   an evaluating unit;
   a breathing gas sensor determining a parameter of respiratory flow, said breathing gas sensor being connected to said breathing gas line and to said evaluating unit, wherein said breathing gas sensor transmits a signal to said evaluating unit;
   an electrochemical propofol sensor with a measuring electrode made of diamond-like carbon, said propofol sensor being in gas flow connection to said breathing gas line and being connected to said evaluating unit; and
   a pump connected to said propofol sensor, wherein said pump is actuated by said evaluating unit for sampling breathing gas based on said signal from said breathing gas sensor and said propofol sensor sending a measured signal for a concentration of propofol to said evaluating unit, wherein said electrochemical propofol sensor comprises electrodes including said measuring electrode and an electrolyte, said electrolyte comprising sulfuric acid or lithium chloride and said electrolyte includes a mediator comprising one or more compounds containing tetravalent cerium which reacts selectively with propofol (2,6-diisopropylphenol) and forms a reaction product that accumulates over one or more samples, said reaction product being determined electrochemically at said measuring electrode.

10. A measuring system in accordance with claim 9, further comprising: an adsorption filter with a heating means arranged upstream of said propofol sensor.

11. A measuring system in accordance with claim 10, wherein said filter comprises Tenax or activated carbon.

12. A measuring system in accordance with claim 9, wherein said measuring electrode can be switched on and off at points in time preset by said evaluating unit.

13. A measuring system in accordance with claim 9, wherein said breathing gas sensor is a sensor of at least one of $CO_2$ sensor, an $O_2$ sensor, a volume flow sensor or a temperature sensor, so that depending on a measured signal of said breathing gas sensor, which is a property of a respiratory flow, reproducible breathing gas samples are delivered into said propofol sensor from said respiratory flow for actuating said pump.

14. A measuring system in accordance with claim 9, wherein said breathing gas sensor receives respiration parameters of a respiration unit of an anesthesia apparatus or respirator and actuates said pump for breathing gas sampling via said evaluating unit especially such that said propofol sensor measures an end tidal propofol concentration in a respiratory flow breathed out.

15. A measuring system in accordance with claim 9, wherein said evaluating unit is connected to at least one dosing device for an intravenous administration of propofol as a function of a current measured signal of said propofol sensor.

16. A measuring system in accordance with claim 15, wherein said evaluating unit is provided with minima and/or maxima for a dosing of a total quantity of propofol and/or per unit of time for a patient.

* * * * *